United States Patent
Mukaide

(10) Patent No.: US 10,444,164 B2
(45) Date of Patent: Oct. 15, 2019

(54) OBJECT INFORMATION ACQUISITION METHOD AND OBJECT INFORMATION ACQUISITION APPARATUS

(71) Applicant: CANON KABUSHIKI KAISHA, Tokyo (JP)

(72) Inventor: Taihei Mukaide, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 244 days.

(21) Appl. No.: 15/312,751

(22) PCT Filed: Jun. 2, 2015

(86) PCT No.: PCT/JP2015/002800
§ 371 (c)(1),
(2) Date: Nov. 21, 2016

(87) PCT Pub. No.: WO2015/190068
PCT Pub. Date: Dec. 17, 2015

(65) Prior Publication Data
US 2017/0146468 A1    May 25, 2017

(30) Foreign Application Priority Data
Jun. 12, 2014 (JP) .................................. 2014-121637

(51) Int. Cl.
*G01N 23/083* (2018.01)
*G01N 23/046* (2018.01)
*G01N 23/207* (2018.01)

(52) U.S. Cl.
CPC ......... *G01N 23/083* (2013.01); *G01N 23/046* (2013.01); *G01N 23/207* (2013.01); *G01N 2223/304* (2013.01); *G01N 2223/419* (2013.01)

(58) Field of Classification Search
CPC .......................... G01N 23/083; G01N 23/046
(Continued)

(56) References Cited

U.S. PATENT DOCUMENTS 8,214,158 B2    7/2012    Mukaide et al. ............... 702/28
8,509,382 B2    8/2013    Mukaide et al. ............... 378/62
(Continued)

FOREIGN PATENT DOCUMENTS

JP        3864262        12/2006
JP        4512660        7/2010
WO    WO 2014/073462 A    5/2014

OTHER PUBLICATIONS

"Assessing the effect of electron density in photon dose calculations", J. Seco et al, Med. Phys. vol. 33 (2), pp. 540-552. Published Jan. 31, 2006 (Year: 2006).*
(Continued)

*Primary Examiner* — Eman A Alkafawi
(74) *Attorney, Agent, or Firm* — Venable LLP

(57) ABSTRACT

Provided is a method for acquiring information relating to a composition of a detected object from results of a measurement, using radiation, this method including: a step for acquiring by a computer a result of measuring the detected object using radiation; a step for estimating by a computer a chemical composition ratio of the detected object, using an equation that contains a value derived from the measurement result as a constant and contains a value derived from the chemical composition ratio of the detected object as a variable, and then solving the equation; and a step for outputting the estimated chemical composition ratio or a physical property value acquired based on the estimated chemical composition ratio as information relating to the composition of the detected object.

18 Claims, 7 Drawing Sheets

(58) Field of Classification Search
USPC .......................................................... 702/28
See application file for complete search history.

(56) References Cited

U.S. PATENT DOCUMENTS

| | | | |
|---|---|---|---|
| 8,532,257 B2 | 9/2013 | Mukaide et al. | ............... 378/62 |
| 8,588,366 B2 | 11/2013 | Mukaide et al. | ............... 378/62 |
| 9,234,856 B2 | 1/2016 | Mukaide | ................ G01N 23/23 |
| 9,700,275 B2 * | 7/2017 | Stampanoni | ........... A61B 6/483 |
| 2010/0278304 A1 | 11/2010 | Mukaide et al. | ............... 378/53 |
| 2015/0103970 A1 * | 4/2015 | Chen | .................... G01N 23/046 |
| | | | 378/5 |

OTHER PUBLICATIONS

"Quantitative grating-based x-ray dark-field computed tomography", Zhen-Tian Wang et al, Department of Engineering Physics, Tsinghua University, Beijing China and Key Laboratory of Particle and Radiation Imaging, Tsinghua University, Ministry of Education, China, Pub. May 9, 2009 (Year: 2009).*

Z. Qi et al., "Quantitative Imaging of Electron Density and Effective Atomic Number Using Phase Contrast CT", *Physics in Medicine and Biology*, Institute of Physics Publishing, vol. 55, No. 9, pp. 2669-2677 (May 7, 2010).

M.S. Nielsen et al., "X-ray Tomography Using the Full Complex Index of Refraction", *Physics in Medicine and Biology*, Institute of Physics Publishing, vol. 57, No. 19, pp. 5971-5979 (Sep. 11, 2012).

Office Action dated Nov. 14, 2017 in counterpart Japanese patent application 2014-121637, with translation.

* cited by examiner

OBJECT INFORMATION ACQUISITION METHOD AND OBJECT INFORMATION ACQUISITION APPARATUS

TECHNICAL FIELD

The present invention relates to a technology for acquiring information on an object from the results of a measurement using radiation.

BACKGROUND ART

Technologies are known that use radiation to analyze or inspect an object (referred to as a detected object). Among these, since X-rays are electromagnetic waves having energy of about 100 eV or more, non-destructive inspection methods using X-rays are used in a wide range of fields from industrial uses to medical uses.

For example, techniques have been proposed for quantitatively obtaining physical property values of detected objects by utilizing the absorption or phase shift of X-rays attributable to the detected object.

PTL1 describes a method for acquiring information on electron density distribution or effective atomic number distribution of a detected object from two or more X-ray absorption-contrast images by utilizing monochromatic X-rays having two or more energy levels (wavelengths).

In addition, PTL2 describes a method for acquiring effective atomic number distribution of a detected object from information on X-ray absorption and phase shift attributable to the detected object.

CITATION LIST

Patent Literature

[PTL 1]
Japanese Patent No. 3864262
[PTL 2]
Japanese Patent No. 4512660

SUMMARY OF INVENTION

Technical Problem

However, the information obtained with the methods of PTL1 and PTL2 consists only of electron density distribution and effective atomic number distribution. For example, although there is a need to obtain information relating to the material (composition) of a detected object in fields such as analysis apparatuses, inspection apparatuses or diagnostic apparatuses, the material of a detected object cannot be identified by conventional methods (namely, with electron density distribution and effective atomic number distribution alone).

With the foregoing in view, an object of the present invention is to provide a novel technology for acquiring more detailed information relating to the composition of a detected object from the results of a measurement using radiation.

Solution to Problem

A first aspect of the present invention provides an object information acquisition method for acquiring information relating to a composition of a detected object from result of a measurement using radiation, the method including: a step for acquiring by a computer a result of measuring the detected object using radiation; a step for estimating by a computer a chemical composition ratio of the detected object, using an equation that contains a value derived from the measurement result as a constant and contains a value derived from the chemical composition ratio of the detected object as a variable, and then solving the equation; and a step for outputting the estimated chemical composition ratio or a physical property value acquired based on the estimated chemical composition ratio as information relating to the composition of the detected object, wherein the value derived from the measurement result includes an absorption characteristic value, which is a value relating to absorption characteristics of the detected object with respect to radiation, and a phase characteristic value, which is a value relating to refraction characteristics of the detected object with respect to radiation.

A second aspect of the present invention provides a program that executes each step of the object information acquisition method according to the present invention with a computer.

A third aspect of the present invention provides an object information acquisition apparatus for acquiring information relating to a composition of a detected object from a result of a measurement using radiation, the apparatus including: an acquisition unit that acquires a result of measuring the detected object, using radiation; an estimation unit that estimates a chemical composition ratio of the detected object, using an equation that contains a value derived from the measurement result as a constant and contains a value derived from the chemical composition ratio of the detected object as a variable, and then solves the equation; and an output unit that outputs the estimated chemical composition ratio or a physical property value acquired based on the estimated chemical composition ratio as information relating to the composition of the detected object, wherein the value derived from the measurement result includes an absorption characteristic value, which is a value relating to absorption characteristics of the detected object with respect to radiation, and a phase characteristic value, which is a value relating to refraction characteristics of the detected object with respect to radiation.

A fourth aspect of the present invention provides a system, which has: a measurement apparatus that measures a detected object using radiation, and the object information acquisition apparatus according to the present invention, which acquires information relating to the composition of the detected object using the measurement result of the measurement apparatus.

A fifth aspect of the present invention provides an object information acquisition method for acquiring information relating to a composition of a detected object from a measurement result of the detected object acquired by irradiating the detected object with X-rays and detecting the X-rays that pass through the detected object, the method including: a step for acquiring by a computer a result of measuring the detected object using X-rays; a step for estimating by a computer a chemical composition ratio of the detected object, using an equation that contains a value derived from the measurement result as a constant and contains a value derived from the chemical composition ratio of the detected object as a variable, and then solving the equation; and a step for outputting the estimated chemical composition ratio or a physical property value acquired based on the estimated chemical composition ratio as information relating to the composition of the detected object.

A sixth aspect of the present invention provides a system, which has: a measurement apparatus that measures a detected object by irradiating the detected object with X-rays and detecting the X-rays that pass through the detected object; and an object information acquisition apparatus that acquires information relating to a composition of the detected object, using a measurement result of the measurement apparatus, wherein the object information acquisition apparatus has an acquisition unit that acquires the result of measuring the detected object using X-rays; an estimation unit that estimates a chemical composition ratio of the detected object, using an equation that contains a value derived from the measurement result as a constant and contains a value derived from the chemical composition ratio of the detected object as a variable, and then solves the equation; and an output unit that outputs the estimated chemical composition ratio or a physical property value acquired based on the estimated chemical composition ratio as information relating to the composition of the detected object.

Advantageous Effects of Invention

According to the present invention, more detailed information relating to the composition of a detected object can be acquired from the result of a measurement using radiation.

Further features of the present invention will become apparent from the following description of exemplary embodiments with reference to the attached drawings.

DESCRIPTION OF EMBODIMENTS

The present invention relates to a technology for acquiring information relating to the composition of a detected object from the result of a measurement using radiation, and further relates to a technology for estimating the chemical composition ratio of a detected object based on a value derived from the result of measurement using radiation. This technology can be preferably applied to, for example, an analysis apparatus for analyzing and identifying a target object, an inspection apparatus for carrying out non-destructive inspections on an object, or a diagnostic apparatus for diagnosing a living body or pathology specimen.

Estimation of chemical composition ratio is carried out by using an equation that contains a value derived from the measurement result of a detected object (value obtained from a measured value) and contains the chemical composition ratio of the detected object (unknown value or variable) followed by solving the equation. A specific method for solving the equation will be subsequently described. Moreover, in the embodiments to be subsequently described, at least one piece of information (physical property value) among mass absorption coefficient with respect to radiation, effective atomic number, mass density, mean atomic number, mean atomic weight and electron density is also acquired as information relating to the composition of the detected object.

The following provides an explanation of a method for estimating the chemical composition ratio of a detected object from an X-ray two-dimensional projection image (first embodiment) and a method for estimating the chemical composition ratio of a detected object from an X-ray CT image (second embodiment) as specific examples of the present invention.

First Embodiment

In a first embodiment of the present invention, a method is explained for acquiring the chemical composition ratio from a two-dimensional projection image of X-rays that have passed through a detected object.

(System Configuration)

Figure 1:
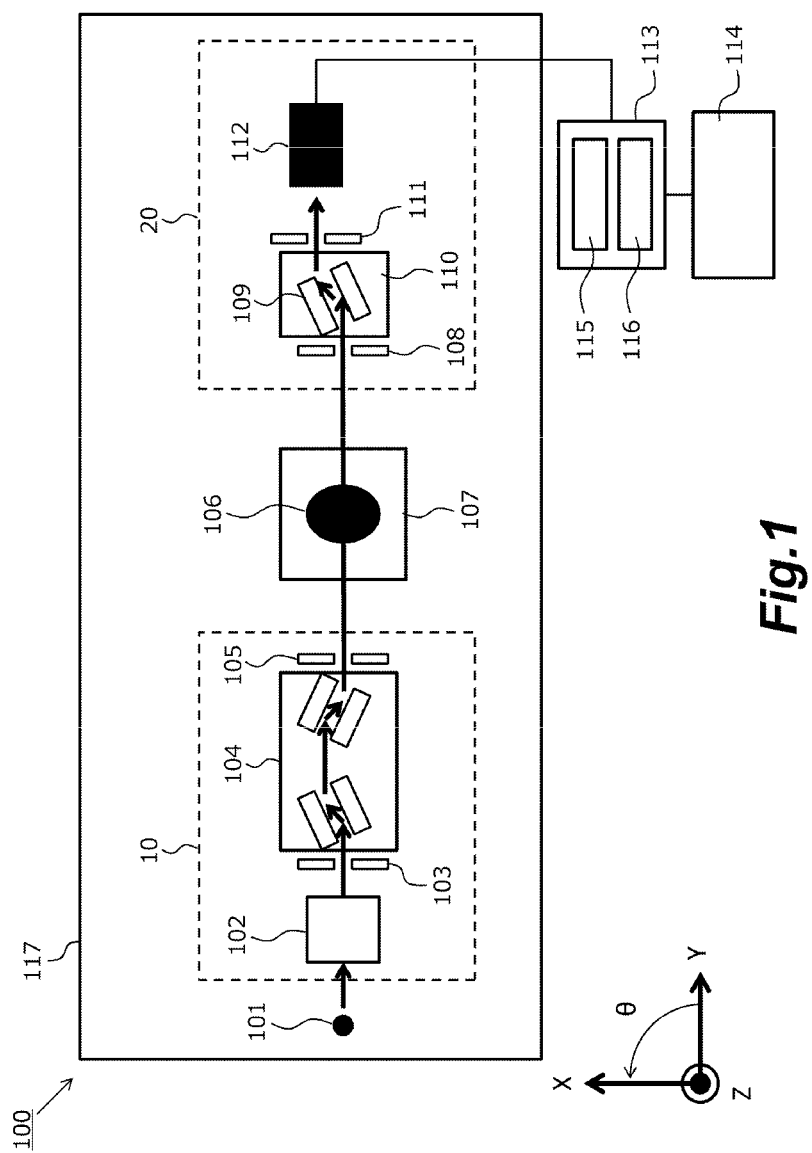
FIG. 1 is a schematic diagram of an X-ray measurement system according to an embodiment.

FIG. 1 shows an example of the configuration of an X-ray measurement system 100 that uses X-rays as an embodiment of a radiation measurement system of the present invention. The X-ray measurement system 100 is provided with an X-ray measurement apparatus 117, which measures a detected object 106 using X-rays, an arithmetic processing apparatus 113, which acquires information relating to the composition of the detected object 106 based on a measurement result of the X-ray measurement apparatus 117, and a display device 114.

The X-ray measurement apparatus 117 is provided with an X-ray radiation unit 10 that forms X-rays from an X-ray source 101 and radiates the X-rays onto the detected object 106, a detected object stage 107 capable of holding and moving the detected object 106, and an X-ray measurement unit 20 that measures X-rays that have passed through the detected object 106. The detailed configuration of each unit will be subsequently described. A measurement result obtained with the X-ray measurement unit 20 is output to the arithmetic processing apparatus 113.

The arithmetic processing apparatus 113 has an arithmetic processing unit 115 and a storage unit 116. The arithmetic processing unit 115 has a function (an acquisition unit) that acquires a measurement result from the X-ray measurement unit 20. Furthermore, the arithmetic processing unit 115 may accept measurement results directly from the X-ray measurement unit 20 or read measurement results accumulated in the storage unit 116. In addition, the arithmetic processing unit 115 has a function that calculates values relating to absorption and phase changes of X-rays attributable to the detected object 106 using the acquired measurement results, and a function (an estimation unit) that estimates the chemical composition ratio of the detected object 106 using values relating to absorption and phase change. In addition, the arithmetic processing unit 115 has a function that acquires other physical property values (such as mass density) based on the estimated chemical composition ratio, and a function (an output unit) that outputs the determined chemical composition ratio and physical property values as information relating to the composition of the detected object. The storage unit 116 has a function that stores data such as measurement results of the X-ray measurement apparatus 117 or physical property values of the detected object 106 acquired by the arithmetic processing unit 115. In the present embodiment, the object information acquisition apparatus is composed by the arithmetic processing apparatus 113.

The arithmetic processing apparatus 113 can be configured with a general-purpose computer having hardware resources such as a central processing unit (CPU), memory, auxiliary storage device (such as a hard drive), input device or communications interface (I/F). The functions of the arithmetic processing unit 115 are realized by the CPU loading and executing a program stored in the auxiliary storage device. In addition, the functions of the storage unit 116 are realized by memory or auxiliary storage device. Furthermore, all or a portion of the functions provided by the arithmetic processing apparatus 113 may also be realized by a circuit such as an field-programmable gate array (FPGA) or application-specific integrated circuit (ASIC). In addition, the arithmetic processing apparatus 113 may also store a program relating to operation and control of the X-ray measurement apparatus 117 and control X-ray measurement of the X-ray measurement apparatus 117 in accordance with that program.

(Estimation of Chemical Composition Ratio)

Next, an explanation is provided of the method used to estimate chemical composition ratio in the first embodiment.

Absorption of X-rays by a substance is represented with Equation (1).

[Math. 1]

$$I = I_0 e^{-\mu t} \quad (1)$$

I represents transmitted X-ray intensity, $I_0$ represents incident X-ray intensity, $\mu$ represents the linear absorption coefficient, and t represents the optical path length of X-rays in a detected object.

Here, transmitted X-ray intensity I is the intensity of X-rays that have passed through the detected object, incident X-ray intensity $I_0$ is the intensity of X-rays measured in the absence of a detected object, and either of these values can be obtained from X-ray measurement results. Thus, the product $\mu t$ of the linear absorption coefficient $\mu$ and the optical path length t of X-rays in the detected object can be determined from Equation (2) based on X-ray measurement results (I and $I_0$). Furthermore, $\mu t$ is a value relating to the X-ray absorption characteristics of the detected object, and will be hereinafter referred to as the absorption characteristic value. In addition, the ratio of $I/I_0$ of transmitted X-ray intensity to incident X-ray intensity is referred to as X-ray transmittance.

[Math. 2]

$$\mu t = \ln\left(\frac{I_0}{I}\right) \quad (2)$$

Next, a description is provided of X-ray refraction (phase shift). X-rays are subjected to refraction when they pass through a substance. The relationship between the angle of refraction ($\Delta\theta$) of the X-rays at this time and, for example, the phase gradient ($\partial\phi/\partial x$) in the X direction orthogonal to the optical axis of X-rays is represented with Equation (3). $\lambda$ represents the wavelength of the X-rays (known value).

[Math. 3]

$$\frac{\partial \phi}{\partial x} = \frac{2\pi}{\lambda} \Delta\theta \quad (3)$$

The value of the angle of refraction $\Delta\theta$ at each point of a detected object can be obtained from X-ray measurement results. Thus, by determining on the basis of Equation 3 the phase gradient at each point of a detected object and integrating those values in the X direction, the amount of the phase shift $\phi$ can be obtained at each point of the detected object. Furthermore, the amount of the phase shift $\phi$ is a value relating to the phase change of X-rays in a detected object (refraction characteristics), and will hereinafter be referred to as the phase characteristic value.

On the other hand, the linear absorption coefficient $\mu$ of a substance can be represented with Equation 4 using the mass density $\rho$ of the substance, Avogadro's number $N_A$, photon interaction cross-section per atom $\sigma_a$ and mean atomic weight $\langle A \rangle$.

[Math. 4]

$$\mu = \rho N_A \frac{\sigma_a}{\langle A \rangle} \quad (4)$$

When represented in this manner, the amount of phase shift $\phi$ can be represented with Equation 5 using the substance mass density $\rho$, Avogadro's number $N_A$, classical electron radius $r_0$, X-ray wavelength $\lambda$, mean atomic weight $\langle A \rangle$, mean atomic number $\langle Z \rangle$ and X-ray optical path length t in the substance.

[Math. 5]

$$\phi = r_0 \lambda \rho t N_A \frac{\langle Z \rangle}{\langle A \rangle} \quad (5)$$

Equation (6) can then be obtained by deleting $\rho$ from Equations (4) and (5) and rearranging the equations.

[Math. 6]

$$\frac{\mu t}{\phi} = \frac{1}{r_0 \lambda} \frac{\sigma_a}{\langle Z \rangle} \quad (6)$$

Since the right side of Equation (6) does not contain the mass density ($\rho$) and the X-ray optical path length (t) of the detected object, it is an amount that can be calculated provided that the chemical composition of the detected object is known. On the other hand, as indicated in Equations (2) and (3), the left side of Equation (6) is an amount that can be calculated from X-ray transmittance and the amount of phase shift obtained from X-ray measurement results.

As has been described above, estimation (identification) of the chemical composition ratio of a detected object can be perceived as the problem of solving an equation obtained by entering a value derived from the results of X-ray measurement into the left side of Equation (6) (or in other words, an equation in which the left side of Equation (6) is a constant and the right side is a variable). Furthermore, although the absorption characteristic value is divided by the phase characteristic value in Equation (6), the numerator and denominator of Equation (6) may be interchanged (or in other words, the phase characteristic value may be divided by the absorption characteristic value).

However, since numerous combinations exist for the chemical composition ratio of a detected object and measurement results contain measurement error, it is not realistic to solve the above-mentioned equation directly. For this reason, in the present embodiment, a highly probable chemical composition ratio is estimated by a procedure for determining an approximate solution of the above-mentioned equation.

More specifically, a procedure is performed in which a candidate is searched for that satisfies a prescribed condition for error among a plurality of candidates (candidate solutions) for the chemical composition ratio. An evaluation function E, which is used to evaluate the error of a candidate solution, can be defined using the values on the left side and the values on the right side of Equation (6). For example, in the case of designating the values on the left side of Equation (6) (namely, values derived from measurement results) as Vobs and the values on the right side of Equation (6) (namely, values derived from the candidate solution) as Vcal, the following equation (7) or (8) can be used preferably.

[Math. 7]

$$E = |V_{obs} - V_{cal}| \quad (7)$$

or

[Math. 8]

$$E = \left| \frac{V_{obs} - V_{cal}}{V_{obs}} \right| \quad (8)$$

In the case of using these evaluation functions, chemical composition ratios are searched for such that the value of the evaluation function (evaluation value) E is equal to or less than a prescribed threshold value TH. A suitable value determined by experimentation and the like may be determined in advance for the threshold value TH. Furthermore, if error is normalized by measured values (Vobs) in the manner of Equation (8), since the effects of measurement conditions (such as X-ray intensity or sensitivity) and physical properties of the detected object can be canceled out, there is the advantage of being able to stably evaluate error with the same threshold value TH regardless of the measurement conditions or detected object.

Any method can be used to search for the approximate solution. Examples thereof include a method involving registering a large number of chemical substances in a database and then collating with that database, and a method involving searching for the chemical composition ratio of each element using a search algorithm. Although specific examples of algorithms that can be applied include the Monte Carlo method, simulated annealing and genetic algorithm, any technique may be used for the search algorithm without any particular limitations thereon.

(Processing of Arithmetic Processing Unit)

Figure 2:
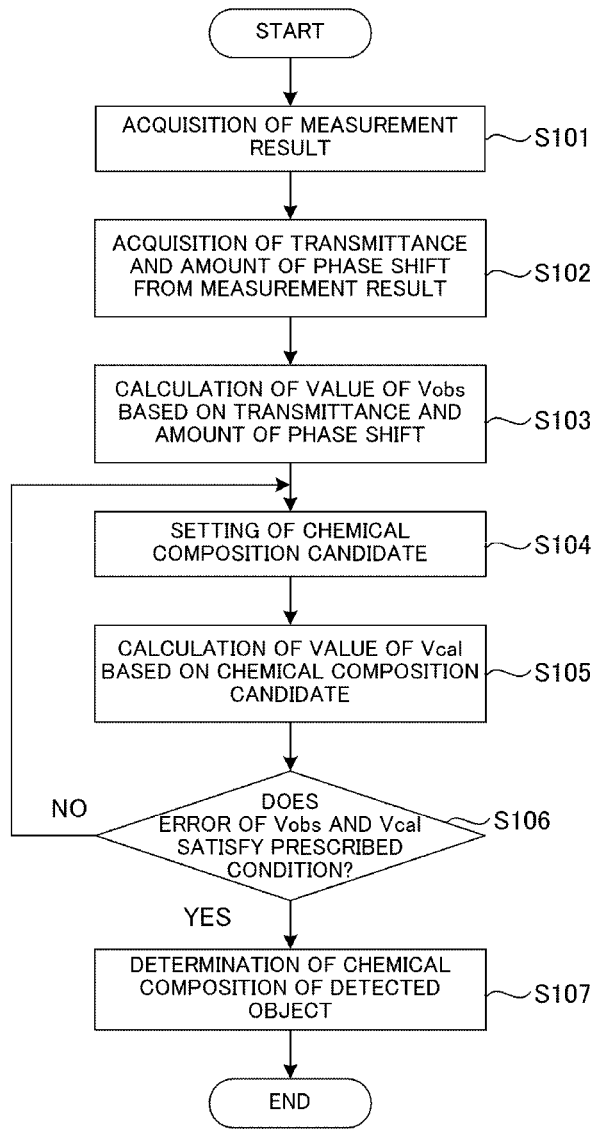
FIG. 2 is an arithmetic processing flow chart of an arithmetic processing apparatus according to Embodiment 1.

FIG. 2 indicates an example of the arithmetic processing flow carried out by the arithmetic processing unit 115 of the arithmetic processing apparatus 113. The example of FIG. 2 is an example of processing in which chemical composition ratios of chemical substances registered in a database are collated in order followed by searching for the chemical composition ratio that most closely coincides with measurement results.

First, the arithmetic processing unit 115 acquires an X-ray measurement result (two-dimensional projection image) of a detected object from the X-ray measurement apparatus 117 (Step S101). Next, the arithmetic processing unit 115 calculates X-ray transmittance ($I/I_0$) and the amount of phase shift ($\phi$) from the X-ray measurement result of the detected object (Step S102). There are various methods for acquiring the amount of phase shift. For example, the X-ray angle of refraction is measured by diffraction enhanced imaging (DEI) using an analyzer crystal, X-ray coherent diffraction microscopy or the Talbot method, and the amount of phase shift is calculated by integrating the phase gradient. Next, the arithmetic processing unit 115 calculates from the X-ray transmittance and the amount of phase shift the value Vobs on the left side of Equation (6) (values of constant terms of the equation) (Step S103).

The arithmetic processing unit 115 then selects a candidate for the chemical composition of the detected object from the database (Step S104), and calculates the value Vcal of the right side of Equation (6) from the candidate chemical composition (Step S105). The arithmetic processing unit 115 then determines whether the error in the value Vobs derived from the measurement result and the error in the value Vcal derived from the chemical composition of the candidate satisfy a preset condition (and in this case, evaluation value E≤threshold value TH as determined using Equation (7) or Equation (8)) (Step S106). In the case where a candidate has been found that satisfies the condition, the arithmetic processing unit 115 uses that candidate as the chemical composition of the detected object and processing ends (Step S107). In the case where the condition is not satisfied, the arithmetic processing unit 115 reads another candidate from the database and repeats the same processing (Steps S104 to S106).

According to the above-mentioned processing, the chemical composition ratio of a detected object can be estimated based on the results of X-ray measurement. Arithmetic processing for estimating chemical composition ratio in the present embodiment can be carried out for each pixel of the X-ray measurement result in the form of a two-dimensional projection image. Alternatively, arithmetic processing for estimating chemical composition ratio can also be carried out for each of a plurality of adjacent pixel groups (obtained by, for example, dividing into pixel groups of a predetermined size in the manner of a 4×4 matrix or gathering together into adjacent pixel groups having similar values for $\mu t/\phi$). A distribution of chemical composition ratios estimated for each pixel or each pixel group, namely chemical composition ratios of a detected object on a projection image, can be output in the form of two-dimensional image data. This two-dimensional image data is also referred to as a chemical composition ratio map.

Furthermore, although the present embodiment has provided an explanation of an aspect in which the chemical composition ratio of a detected object is estimated on the basis of X-ray measurement results, the chemical composition ratio of a detected object can also be estimated based on γ-ray measurement results using a similar system. In addition, other types of radiation can also be used provided that it enables absorption characteristic value ($\mu t$)/phase characteristic value ($\phi$) to be indicated with a value able to be acquired from the chemical composition ratio. For example, the same relational expression (expression corresponding to Equation (6)) can be derived in the same manner as in the present embodiment even if using electron beam or neutron radiation, and chemical composition ratio can be acquired from the derived relational expression.

Second Embodiment

In a second embodiment of the present invention, an explanation is provided of a technique that uses computed tomography (CT). CT refers to a technique for reconstructing information on a tomographic image from information on a plurality of projection images measured while changing the direction in which radiation is projected. The same configuration as indicated in the first embodiment (see FIG. 1) can be used for the configuration of the radiation measurement system.

(Estimation of Chemical Composition Ratio)

The following provides an explanation of the method used to estimate chemical composition ratio in the second embodiment.

The complex refractive index ($n=1-\delta-i\beta$) of a detected object with respect to X-rays can be acquired from X-ray absorption information and phase information by using X-ray CT. The imaginary component $\beta$ of the complex refractive index is a value relating to X-ray absorption characteristics of the detected object, and is hereinafter referred to as absorption characteristic value. The absorption characteristic value $\beta$ can be acquired by CT configuration of measurement results in the form of absorption information. On the other hand, a portion of the real component $\delta$ of complex refractive index is a value relating to a phase change (refraction characteristics) of X-rays attributable to a detected object, and is hereinafter referred to as phase characteristic value. The phase characteristic value $\delta$ can be acquired by CT reconstruction of measurement results in the form of phase information.

However, the absorption characteristic value $\beta$ of a substance can be represented with Equation (9) using X-ray wavelength $\lambda$, mass density $\rho$ of the substance, Avogadro's number $N_A$, photon interaction cross-section per atom $\sigma_a$ and mean atomic weight $\langle A \rangle$, while phase characteristic value $\delta$ can be represented with Equation (10) using X-ray wavelength $\lambda$, mass density $\rho$ of the substance, Avogadro's number $N_A$, classical electron radius $r_0$, mean atomic weight $\langle A \rangle$ and mean atomic number $\langle Z \rangle$.

[Math. 9]

$$\beta = \frac{\lambda}{4\pi} \rho N_A \frac{\sigma_a}{\langle A \rangle} \tag{9}$$

[Math. 10]

$$\delta = \frac{\rho r_0 \lambda^2 N_A}{2\pi} \frac{\langle Z \rangle}{\langle A \rangle} \tag{10}$$

$\rho_\beta$ and $\rho_\delta$ can be represented with Equation (11) by defining mass density in Equation (9) as $\rho_\beta$ and defining mass density in Equation (10) as $\rho_\delta$.

[Math. 11]

$$\begin{cases} \rho_\beta = \beta \Big/ \left( \frac{\lambda}{4\pi} N_A \frac{\sigma_a}{\langle A \rangle} \right) \\ \rho_\delta = \delta \Big/ \left( \frac{r_0 \lambda^2 N_A}{2\pi} \frac{\langle Z \rangle}{\langle A \rangle} \right) \\ \rho_\beta = \rho_\delta \end{cases} \tag{11}$$

In Equation (11), the values of the denominator on the right side of the first equation and the second equation (namely, $\sigma_a/\langle A \rangle$ and $\langle Z \rangle/\langle A \rangle$) can be calculated provided that the chemical composition of the detected object is known. On the other hand, the values of the numerator on the right side of the first equation and the second equation (namely, $\beta$ and $\delta$) can be calculated from the measurement results of X-ray CT as previously described. Thus, estimation (identification) of the chemical composition ratio of a detected object can be perceived as the problem of solving a simultaneous equation in which the values of $\beta$ and $\delta$ derived from measurement results are entered into the first equation and the second equation of Equation (11).

In the present embodiment as well, estimation of the chemical composition of a detected object is carried out by a procedure whereby the approximate solution of the above-mentioned simultaneous equation is determined in the same manner as in the first embodiment. The evaluation function E in this case can be defined using the difference between the value of mass density $\rho_\beta$ calculated from the absorption characteristic value $\beta$ and the value of mass density $\rho_\delta$ calculated from the phase characteristic value $\delta$. For example, Equation (12) or Equation (13) can be used preferably.

[Math. 12]

$$E = |\rho_\delta - \rho_\beta| \tag{12}$$

or

[Math. 13]

$$E = \left| \frac{\rho_\delta - \rho_\beta}{\rho_\delta} \right| \tag{13}$$

In the case of using these evaluation functions, chemical composition ratios are searched for such that the evaluation value E is equal to or less than a prescribed threshold value TH. A suitable value determined by experimentation and the like may be determined in advance for the threshold value TH. Furthermore, if error is normalized in the manner of Equation (13), since the effects of measurement conditions (such as X-ray intensity or sensitivity) and physical properties of the detected object can be canceled out, there is the advantage of being able to stably evaluate error with the same threshold value TH regardless of the measurement conditions or detected object.

Any method can be used to search for the approximate solution. Examples thereof include a method involving registering a large number of chemical substances in a database and then collating with that database, and a method involving searching for the chemical composition ratio of each element using a search algorithm. Although specific examples of algorithms that can be applied include the Monte Carlo method, simulated annealing and genetic algorithm, any technique may be used for the search algorithm without any particular limitations thereon.

(Processing of Arithmetic Processing Unit)

Figure 3:
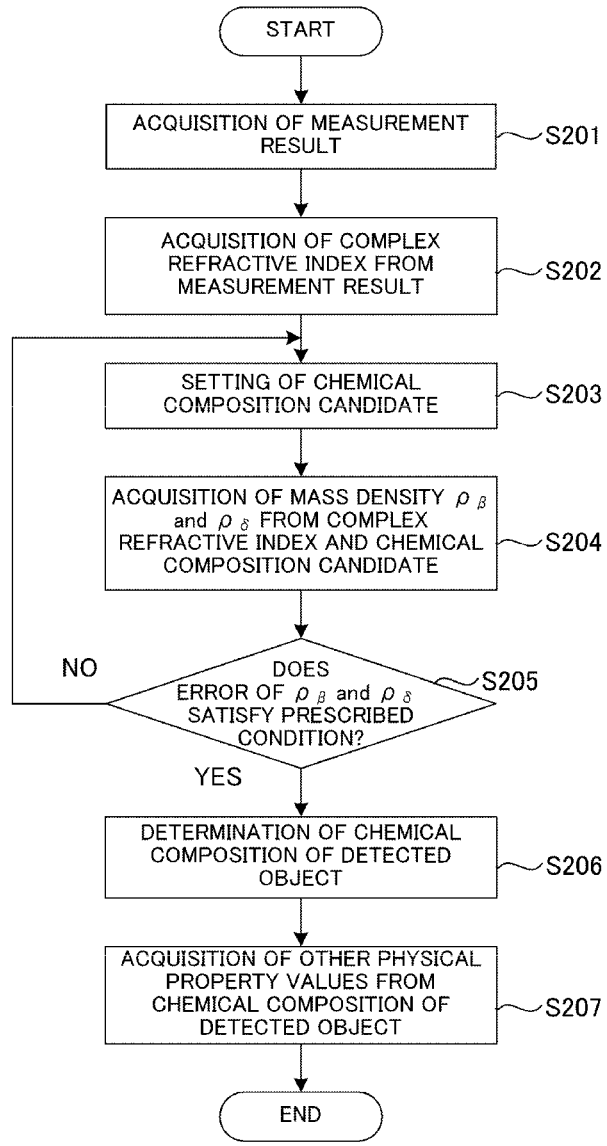
FIG. 3 is an arithmetic processing flow chart of an arithmetic processing apparatus according to Embodiment 2.

FIG. 3 indicates an example of the arithmetic processing flow carried out by the arithmetic processing unit 115 of the arithmetic processing apparatus 113. The example of FIG. 3 is an example of processing in which the approximate solution (optimum solution) that satisfies a prescribed condition is determined using a search algorithm.

First, the arithmetic processing unit 115 acquires an X-ray measurement result (X-ray CT image) of a detected object from the X-ray measurement apparatus 117 (Step S201). Next, the arithmetic processing unit 115 acquires the complex refractive index, namely the values of β and δ, of the detected object from X-ray measurement results of the detected object using a reconstruction algorithm (Step S202). Examples of X-ray CT techniques enabling measurement of changes in absorption and phase shift of X-rays attributable to a detected object include diffraction enhanced imaging (DEI), X-ray coherent diffraction microscopy and the Talbot method. Any technique may be used for the technique used for X-ray CT measurement in the present embodiment provided that it allows the obtaining of information on tomographic images of β and information on tomographic images of δ. In addition, examples of reconstruction algorithms for reconstructing from projection image information to tomographic image information include two-dimensional Fourier transform, filtered back projection and algebraic reconstruction techniques (ART). Any method may be used for the reconstruction algorithm method in the present embodiment provided that it allows the obtaining of tomographic image information.

Next, the arithmetic processing unit 115 sets a candidate for the chemical composition of the detected object (Step S203). The arithmetic processing unit 115 then acquires the candidate chemical composition and mass density $\rho_\beta$ and $\rho_\delta$ from the values of β and δ acquired in Step S202 in accordance with Equation (11) (Step S204). Furthermore, although $\sigma_a$ can be calculated using the photon interaction cross-section per atom of each element from a database, it may also be determined through measurement of a standard sample. The arithmetic processing unit 115 then determines whether the candidate satisfies a preset condition (in this case, E≤threshold value TH) by entering the values of mass density $\rho_\beta$ and $\rho_\delta$ acquired in Step S204 into the evaluation function E (Step S205). In the case where a candidate has been found that satisfies the condition, the arithmetic processing unit 115 uses that candidate as the chemical composition of the detected object and processing ends (Step S206). In the case where the condition is not satisfied, the arithmetic processing unit 115 updates the chemical composition ratio candidate (Step S203) and repeats the same processing.

In the case where a chemical composition ratio that satisfies the condition has been obtained as a result of the search processing described above, the arithmetic processing unit 115 is able to additionally acquire other information relating to the composition of the detected object (Step S207). Examples of other information that can be acquired include mass density of the detected object, mass absorption coefficient of the detected object with respect to X-rays, effective atomic number, mean atomic weight, mean atomic number and electron density. Furthermore, mean atomic number and mean atomic weight can be calculated using an estimated chemical composition. In addition, mass absorption coefficient (μ/ρ) can be obtained from Equation (4) or Equation (9) using an estimated chemical composition. In addition, effective atomic number ($Z_{eff}$) can be obtained from Equation (14) using an estimated chemical composition.

[Math. 14]

$$Z_{eff} = \frac{\sigma_a}{\sigma_e} \quad (14)$$

$\sigma_e$ represents the photon interaction cross-section per electron. In addition, electron density ($\rho_e$) can be obtained from Equation (15) using the value of δ acquired from a measurement result. Alternatively, electron density may be calculated using an estimated chemical composition and mass density instead of the value of δ.

[Math. 15]

$$\rho_e = \frac{2\pi\delta}{r_0 \lambda^2} \quad (15)$$

According to the above-mentioned processing, information relating to the composition of a detected object can be acquired based on a measurement result of X-ray CT. Furthermore, the manner in which the initial value of a candidate is imparted and the manner in which candidates are updated vary according to the search algorithm used. For example, in the case of using a search algorithm to repeatedly calculate a group of candidates (a plurality of candidates) in the manner of a genetic algorithm, a plurality of candidates are generated and updated in Step S203, and the candidate having the smallest evaluation value E among the plurality of candidates is determined in Step S205.

In addition, the following Equation (16) can be obtained by rearranging Equation (11) and deleting mass density $\rho_\beta$ and $\rho_\delta$.

[Math. 16]

$$\frac{\beta}{\delta} = \frac{1}{2\lambda r_0} \frac{\sigma_a}{\langle Z \rangle} \quad (16)$$

An equation in which the values β and δ derived from a measurement result are entered into the left side of Equation (16) may be used instead of the simultaneous equation of Equation (11). In other words, the chemical composition ratio of a detected object can also be estimated by calculating β/δ instead of calculating mass density $\rho_\beta$ and $\rho_\delta$, and using the same processing as that of the first embodiment. In that case, the evaluation function of Equation (7) or Equation (8) can be used by defining the value on the left side of Equation (16) as Vobs and defining the value on the right side as Vcal. Moreover, an evaluation value according to Equation (12) or Equation (13) and an evaluation value according to Equation (7) or Equation (8) may be respectively determined by calculating $\rho_\beta$, $\rho_\delta$, Vobs and Vcal according to Equation (11) and Equation (16), and condition assessment of Step S205 may be carried out according to the sum total of the evaluation values. Furthermore, the numerator and denominator of Equation (16) may be interchanged.

The arithmetic processing for estimating chemical composition ratio of the present embodiment can be carried out for each pixel or each pixel group in an X-ray CT tomographic image. Thus, according to the method of the present embodiment, a three-dimensional distribution of the chemical composition ratio and the like inside of a detected object can be acquired. The three-dimensional distribution of the chemical composition ratio and the like can be output in the form of, for example, a plurality of two-dimensional tomographic image data or three-dimensional voxel data.

Furthermore, although the present embodiment has provided an explanation of an aspect in which the chemical composition ratio of a detected object is estimated based on X-ray measurement results, the chemical composition ratio of a detected object can also be estimated based on γ-ray measurement results using a similar system. In addition, other types of radiation can also be used provided that it enables absorption characteristic value (β)/phase characteristic value (δ) to be indicated with a value able to be acquired from the chemical composition ratio. For example, the same relational expression (expression corresponding to Equations (11) and (16)) can be derived in the same manner as in the present embodiment even if using electron beam or neutron radiation, and chemical composition ratio can be acquired from the derived relational expression.

Third Embodiment

In a third embodiment of the present invention, a restricting condition is set for chemical composition ratio when generating or selecting a candidate of the chemical composition ratio. This is because, by excluding non-existent chemical composition ratios and chemical composition ratios having a low possibility of being a candidate from potential candidates (search range), the estimation accuracy (accuracy rate) of chemical composition ratios is improved and search time is shortened. Although the following indicates examples of a plurality of restricting conditions, any one of these restricting conditions may be set or a plurality of conditions may be set in combination.

(1) Degree of Unsaturation

For example, a restricting condition can be set such that only those chemical compositions in which the degree of unsaturation is an integer are selected as candidates. In the case where presumed constituent elements of a detected object consist of group 16 elements, such as carbon (C), nitrogen (N) or oxygen (O), and hydrogen (H), the degree of unsaturation thereof can be represented with Equation (17).

[Math. 17]

$$\text{Degree of unsaturation} = \frac{2C + 2 - H + N}{2} \quad (17)$$

C, N and H in Equation (17) represent the number of each element. Furthermore, in the case of assuming that the detected object contains other constituent elements, the degree of unsaturation is suitably calculated corresponding to those presumed constituent elements of the detected object.

(2) Nitrogen Rule

The nitrogen rule is a principle which states that, if the number of nitrogen atoms contained in a molecule is even (including 0), then the nominal mass of that compound is an even number, while if the number of nitrogen atoms is odd, then the nominal mass of the compound is odd. A restricting condition may be set such that only those chemical compositions in which nominal mass and the number of nitrogen atoms satisfy the nitrogen rule are selected as candidates by using this rule.

(3) Ratio of Mean Atomic Number to Mean Atomic Weight

Figure 4:
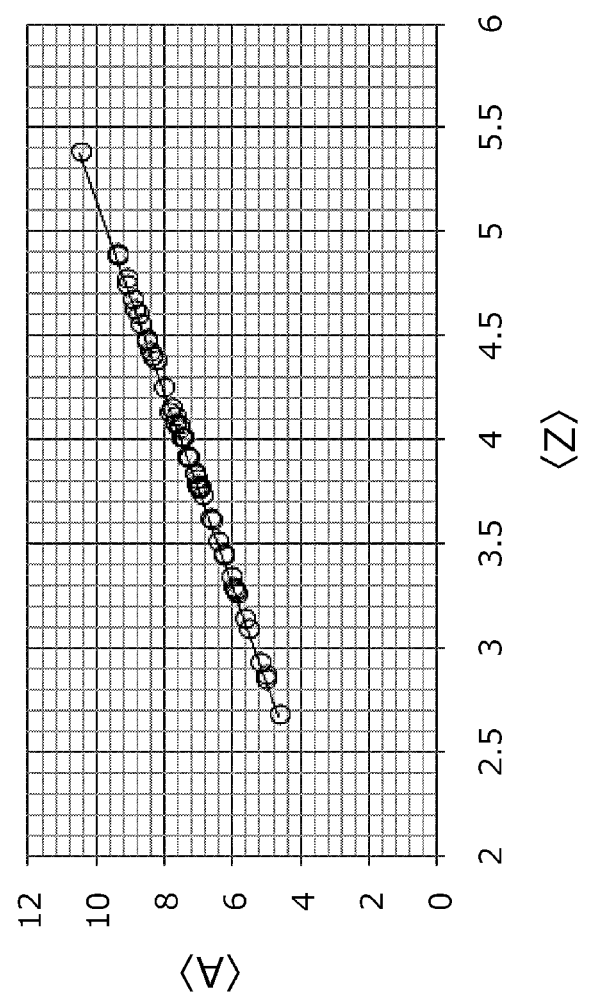
FIG. 4 is a graph representing the relationship of $<A>$ with respect to $<Z>$ of an existing compound.

The following explanation is provided using as an example the case where the presumed constituent elements of a detected object are C, N, O and H. FIG. 4 indicates a graph in which the values of mean atomic weight <A> versus mean atomic number <Z> are plotted for 57 types of existing compounds. As can be understood from the graph, an extremely strong linear correlation is observed between mean atomic number <Z> and mean atomic weight <A>. On the basis thereof, a restricting condition may be used such that compounds in which the relationship between mean atomic number <Z> and mean atomic weight <A> calculated from a chemical composition deviates significantly from the approximation straight line indicated in FIG. 4 are excluded from consideration as candidates. For example, only chemical compositions for which error is within 1% relative to the approximation straight line are used as candidates. Furthermore, the approximation straight line may be determined in advance by experimentation and the like for each presumed constituent element of a detected object.

(4) Hydrogen Ratio

Figure 5:
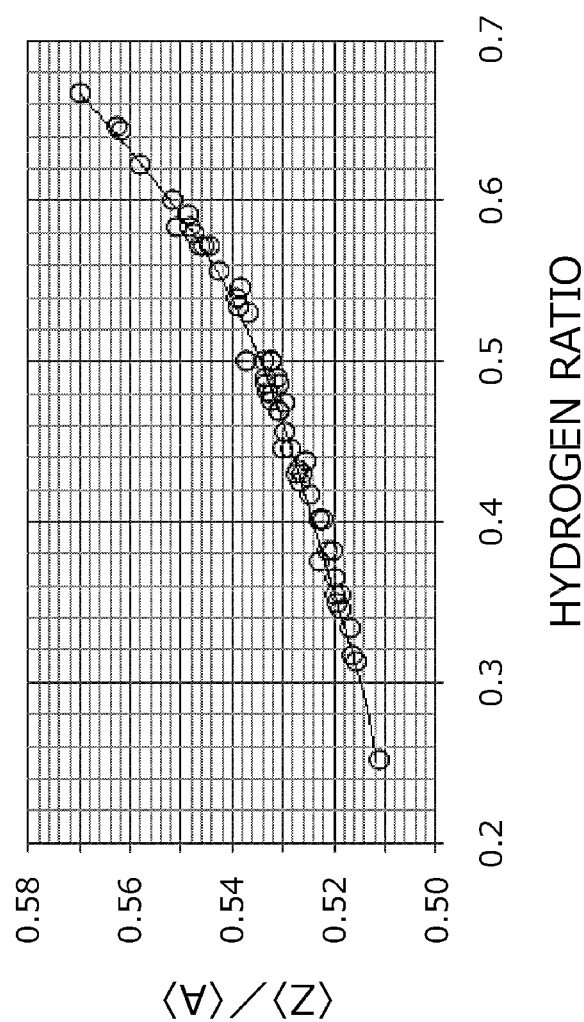
FIG. 5 is a graph representing the relationship of $<Z>/<A>$ with respect to the hydrogen ratio of an existing compound.

FIG. 5 indicates a graph in which the value of <Z>/<A> is plotted versus hydrogen ratio (hydrogen composition ratio) for the same 57 types of existing compounds as in FIG. 4. As can be understood from the graph, both parameters demonstrate an extremely strong correlation. On the basis thereof, a restricting condition can be used such that those compounds in which relationship between hydrogen ratio calculated from chemical composition and the <Z>/<A> deviate significantly from the approximation curve indicated in FIG. 5 are excluded from consideration as candidates. For example, only chemical compositions for which error is within 5% relative to the approximation curve are used as candidates. Furthermore, the approximation curve may be determined in advance by experimentation and the like for each presumed constituent element of a detected object.

(5) Mass Absorption Coefficient

Figure 6:
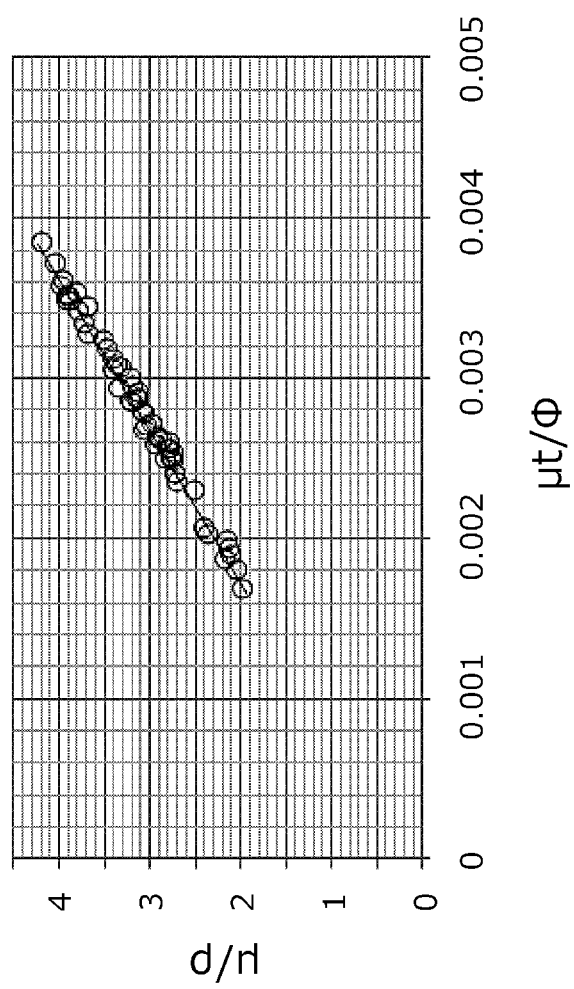
FIG. 6 is a graph representing the relationship of $\mu/\rho$ with respect to $\mu t/\phi$ of an existing compound.

FIG. 6 indicates a graph in which the values of $\mu t/\phi$ and mass absorption coefficient ($\mu/\rho$) are plotted for the same 57 types of existing compounds as in FIG. 4. As can be understood from the graph, both parameters demonstrate an extremely strong correlation. On the basis thereof, a restricting condition can be used such that compounds in which the relationship between $\mu t/\phi$ and $\mu/\rho$ calculated from chemical composition significantly deviate from the approximation curve indicated in FIG. 6 are excluded from consideration as candidates. For example, only chemical compositions for which error is within 5% relative to the approximation curve are used as candidates. $\mu t/\phi$ can be calculated from Equation (6), for example, while $\mu/\rho$ can be calculated from Equation (4), for example. Furthermore, the approximation curve may be determined in advance by experimentation and the like for each presumed constituent element of a detected object.

By applying one or more restricting conditions as described above to the processing of Step S104 of the first embodiment or Step S203 of the second embodiment, non-existent chemical composition ratios and chemical composition ratios having a low possibility of being a candidate can be excluded from consideration as candidates (search range). As a result, the estimation accuracy of chemical composition ratios can be improved and search time can be shortened. Furthermore, restricting conditions other than those indicated here may also be used.

EXAMPLES

Next, an explanation is provided of more specific examples of the above-mentioned embodiments. FIG. 1 may be referred to with respect to the configuration of the X-ray measurement system.

The X-ray measurement system 100 is provided with the X-ray measurement apparatus 117, the arithmetic processing apparatus 113, which acquires information relating to the composition of the detected object 106 based on measurement results of the X-ray measurement apparatus 117, and a display device 114. The X-ray measurement apparatus 117 has the X-ray radiation unit 10, which monochromatizes and forms X-rays from the X-ray source 101 and which emit X-rays to the detected object 106, the detected object stage 107, and the X-ray measurement unit 20, which measures X-ray intensity by refraction of X-rays that have passed through the detected object 106.

An X-ray source 101 of the rotating anticathode type employing a Cu target is used for the X-ray source 101. X-rays generated by the X-ray source 101 are formed by being monochromatized by the X-ray measurement unit 10. Monochromatization refers to a procedure for extracting only those X-rays of a specific energy (wavelength region), while formation refers to a procedure for forming a desired X-ray beam.

The X-ray measurement unit 10 has an X-ray multilayer mirror 102, a slit 103, a 4-crystal monochromator 104 and a collimator 105. The X-ray multilayer mirror 102 carries out monochromatization and condensation of X-rays from the X-ray source 101. Divergent X-rays from the X-ray multilayer mirror 102 are blocked by the slit 103. In the present example, the slit 103 used has a rectangular opening measuring 2 mm in Z direction and 1 mm in the X direction. Furthermore, in FIG. 1, the Y direction is the direction parallel to the optical axis of the X-rays, while the X direction and Z direction are directions perpendicular to the optical axis of the X-rays. The vertical direction and horizontal direction of two-dimensional X-rays obtained with the X-ray measurement apparatus 117 correspond to the X direction and Z direction, respectively.

The 4-crystal monochromator 104 suppresses X-ray divergence while improving their monochromaticity. In the 4-crystal monochromator 104, the diffraction plane (220) uses a Ge single crystal. As a result, monochromatized X-rays characteristic of $CuK_{\alpha 1}$ can be used that have low divergence.

X-rays from the 4-crystal monochromator 104 are formed into X-rays having a diameter of 50 μm by the collimator 105. The collimator 105 used is provided with an opening having a diameter of 50 μm in a Pt plate having a thickness of 100 μm. Furthermore, a collimator composed of a material other than Pt having a high X-ray absorption capacity, such as Au, Pb, Ta or W, can also be used for the collimator 105. X-rays formed by the collimator 105 are emitted onto the detected object 106.

In the present example, a PET fiber having a diameter of 3 mm is used for the detected object 106. The detected object 106 is arranged on the detected object stage 107 and immobilized thereon. This detected object stage 107 can be moved back and forth in the X, Y and Z directions, and can be rotated in the X, Y and Z directions by respectively using an axis parallel thereto as the axis of rotation thereof.

X-rays that have passed through the detected object 106 enter the X-ray measurement unit 20. The X-ray measurement unit 20 has a slit 108, an analyzer crystal 109, an analyzer crystal stage 110, a slit 111 and an X-ray detector 112.

X-rays that have passed through the detected object 106 enter the analyzer crystal 109 after having passed through the slit 108. The slit 108 has a rectangular opening measuring 1 mm in the Z direction and 1 mm in the X direction. The analyzer crystal 109 is for extracting only those X-rays that enter at an angle that satisfies diffraction conditions, and the diffraction plane (220) uses a Ge single crystal. The analyzer crystal 109 is installed on the analyzer crystal stage 110 having an axis parallel to the Z direction for the axis of rotation thereof.

X-rays that have been diffracted with the analyzer crystal 109 pass through the slit 111 and the intensity thereof is measured by the X-ray detector 112. The slit 111 is for preventing superfluous X-rays from entering the X-ray detector 112 from the analyzer crystal 109, and has an opening measuring 1 mm in the X direction and 5 mm in the Z direction. In addition, a scintillation counter that uses an NaI crystal is used for the X-ray detector 112.

The angle distribution of the intensity of X-rays that enter the analyzer crystal 109 can be measured by rotating the analyzer crystal 109 with the analyzer crystal stage 110 and measuring (scanning) X-ray intensity over a specific angle range.

Figure 7:
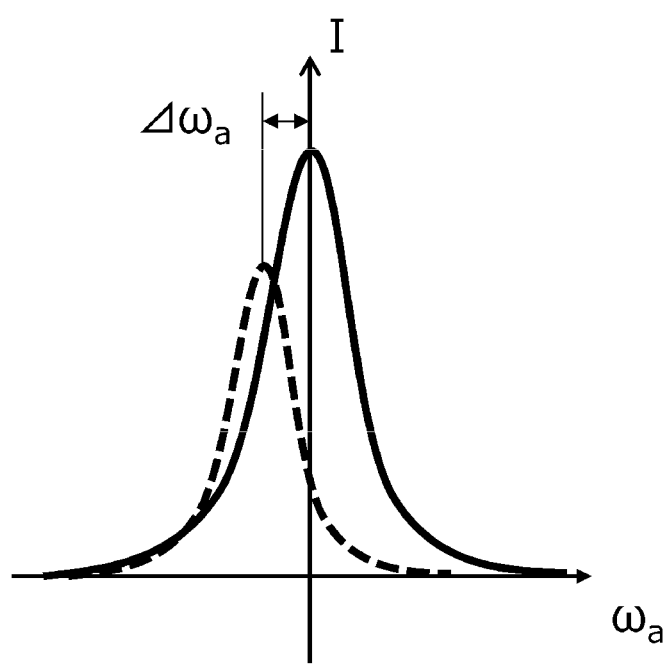
FIG. 7 is a schematic diagram of the angle distribution of X-ray intensity.

FIG. 7 shows a schematic diagram of the angle distribution of X-ray intensity obtained according to this measurement. The rotation angle ($\omega_a$) of the analyzer crystal 109 is plotted on the horizontal axis, while X-ray intensity (I) is plotted on the vertical axis. X-ray intensity depicted with the solid line indicates X-ray intensity in the absence of the detected object 106, while X-ray intensity depicted with the dotted line indicates the intensity of X-rays that have passed through the detected object 106.

The integrated intensity of X-ray intensity depicted with the dotted line is weaker than that of the X-ray intensity depicted with the solid line due to the X-ray-absorbing effect of the detected object 106, and the peak per se shifts by the amount of the refraction angle due to X-ray refraction as a result of a phase shift in the detected object 106. In other words, X-ray transmittance of the portion of the detected object 106 irradiated with X-rays can be obtained from the rate of change in integrated intensity between the dotted line and the solid line, and refraction angle of the portion irradiated by X-rays can be obtained from the amount of the peak shift ($\Delta\omega_a$).

Each point is scanned and measured with the analyzer crystal 109 by moving the detected object stage 107 to move the detected object 106 in the X direction at a 50 μm pitch. Each angle is then measured in the same manner by rotating the detected object 106 about the Z axis (θ rotation) in 1° increments. θ can be measured over a range of 1° to 180°. These measurement results are then transmitted to the arithmetic processing apparatus 113, and the arithmetic processing apparatus 113 acquires X-ray transmittance and refraction angle of the detected object 106 from the measurement results and further acquires information on the tomographic image.

The following provides a detailed explanation of the flow of arithmetic processing carried out by the arithmetic processing apparatus 113.

First, a detailed explanation is provided of a step for acquiring a complex refractive index from the X-ray measurement apparatus 117 (Step S202 in FIG. 2).

Transmittance T(θ,X) is determined by calculating the integrated intensity of the X-rays at each θ from the measurement results and dividing this by integrated intensity in the absence of the detected object 106. X represents the coordinate in the X direction in a sample. μt(θ,X) is acquired at each portion of the detected object 106 from transmittance T using the following Equation (18). This μt(θ,X) is absorption information of the detected object 106 as related to the X-rays.

[Math. 18]

$$\mu t(\theta, X) = -\ln(T(\theta, X)) \qquad (18)$$

Differential phase values are acquired from the refraction angle $\Delta\omega a(\theta,X)$ for each $\theta$ using the following Equation (19).

[Math. 19]

$$\frac{\partial \phi(\theta, X)}{\partial X} = \frac{2\pi}{\lambda}\Delta\omega_a(\theta, X) \quad (19)$$

The amount of the phase shift $\phi(\theta,X)$ in the detected object 106 is obtained by integrating these differential phase values in the X direction. This $\phi(\theta,X)$ is phase information of the detected object 106 as related to the X-rays.

A tomographic image is reconstructed and information on the tomographic image is acquired from the values of $\mu t(\theta,X)$ and $\phi(\theta,X)$ over a range of $\theta$ of 1° to 180° using an ART algorithm. The contrast of the tomographic image obtained from $\mu t(\theta,X)$ is $\mu$, and a tomographic image having an absorption characteristic value $\beta$ is acquired from this value of $\mu$ and the wavelength $\lambda$ of the X-rays using Equation (20).

[Math. 20]

$$\mu = \frac{4\pi}{\lambda}\beta \quad (20)$$

On the other hand, contrast obtained from $\phi(\theta,X)$ is $\phi/t$, and a tomographic image having a phase characteristic value $\delta$ is acquired from this value of $\phi/t$ and the wavelength $\lambda$ of the X-rays using Equation (21).

[Math. 21]

$$\frac{\phi}{t} = \frac{2\pi}{\lambda}\delta \quad (21)$$

Next, a detailed example is indicated of a step for generating and updating candidates for the chemical composition ratio of a detected object (chemical composition candidates) (Step S203 in FIG. 2). In the present example, a genetic algorithm, which is a type of search algorithm, is used. In addition, in the present example, the detected object 106 is assumed to be an organic compound composed of H, C, N and O.

First, 250 chemical composition candidates are generated as first-generation initial candidates by determining the respective numbers of H, C, N and O using random numbers. At this time, the upper limit of the respective number of H, C, N and O in the compound is set at 60, the lower limits of H and C are set at 1, and the lower limits of the remaining elements are set at 0. In addition, the restricting conditions described in the third embodiment are applied. More specifically, in the case where the degree of unsaturation in a chemical composition candidate generated by random numbers is not an integer, or in the case where the chemical composition candidate does not satisfy the nitrogen rule, that chemical composition candidate is discarded and another candidate is newly generated. Moreover, in the case where the difference between the mean atomic weight <A>, obtained by fitting the mean atomic number <Z> calculated from the chemical composition candidate to the approximation straight line shown in FIG. 4, and the mean atomic weight <A> calculated from the chemical composition candidate, is 1% or more, that chemical composition candidate is also discarded and a different candidate is generated.

Next, another 250 candidates are newly generated by applying a genetic procedure to the 250 initial candidates, resulting in a total of 500 candidates being set for the number of chemical composition candidates. Here, genetic information is considered as a group of four numbers composed of the respective numbers of H, C, N and O in the chemical composition. Two candidates are then randomly selected from the 250 initial candidates, and a crossing procedure is carried out in which the numbers of elements are exchanged between the two candidates. Crossing is set to occur at a probability of ¼ for each element. In addition, following the crossing procedure, a mutation procedure is carried out in which the number of any element is reset according to a random number at a probability of ⅓. Two new chemical composition candidates are generated as a result of this genetic procedure. 250 new candidates are then generated by repeating this procedure. Furthermore, a restricting condition is also applied in the case of generating these chemical composition candidates according to this genetic procedure in the same manner as in the case of the initial candidates.

Next, a specific example is indicated of a step for acquiring mass density $\rho_\beta$ and $\rho_\delta$ from the values of $\beta$ and $\delta$ determined from the measurement results and from the chemical composition candidates (Step S204 in FIG. 2).

$\sigma_a$/<A> and <Z>/<A> are calculated for each of the 500 chemical composition candidates. Equation (22) is used to calculate $\sigma_a$.

[Math. 22]

$$\sigma_a = \frac{1}{n}\sum_i n_i \sigma_{ai} \quad (22)$$

Here, n represents the sum of the constituent elements of the chemical composition candidate, and $n_i$ represents the number of each element i. $\sigma_{ai}$ represents the photon interaction cross-section per atom of each element i, and this value is acquired from a database.

Mass density $\rho_\beta$ and $\rho_\delta$ of a chemical composition candidate are then obtained by entering these values and the values of $\beta$ and $\delta$ obtained in Step S202 into the first equation and the second equation of Equation (11). This calculation is carried out for each of the 500 candidates.

Next, a detailed example is indicated of a method for verifying chemical composition (Step S205 in FIG. 2).

Error between mass density $\rho_\beta$ and $\rho_\delta$ is calculated for each of the set 500 chemical composition candidates. In the present example, error E is calculated according to the evaluation function indicated in Equation (13). The 500 chemical composition candidates are then ranked in ascending order starting with the smallest amount of error E. In the case where value of the minimum error Emin is equal to or less than the threshold value TH (set such that TH=1% in the present example), the candidate having that minimum error Emin is judged to be the target chemical composition, and search processing ends. In the case where the minimum error Emin does not satisfy this condition for ending processing (Emin >TH), the chemical composition candidate is updated and processing is repeated. In the present example, since 250 candidates were selected as initial candidates from the current generation of 500 candidates and the above-mentioned genetic procedure was carried out on those candidates, 500 next-generation candidates were generated. Furthermore, although the 250 initial candidates may be selected in any manner, in the present example, 125 candidates were used starting from the candidate with the smallest error, and an additional 125 candidates were randomly selected from the remaining 375 candidates, thereby resulting in the establishment of 250 candidates.

When the number of times processing repeated reaches a prescribed number of processing cycles (set to 1000 processing cycles in the present example) without finding a chemical composition for which error is equal to or less than the threshold value, the chemical composition candidate having the smallest error up to that point is used as the solution. The above-mentioned processing is carried out on those portions (pixels) of a tomographic image where a sample is present, and ultimately four images using the composition ratios of H, C, N and O as contrast are acquired for each pixel.

Next, a specific example is indicated of a step for acquiring physical property values of a detected object (Step S207 in FIG. 2).

An image relating to mass density ($\rho$) is acquired by calculating the mean value of mass density $\rho_\beta$ and $\rho_\delta$ calculated in Step S204 for each pixel. An image relating to effective atomic number ($Z_{eff}$) is obtained by calculating using the chemical composition ratio and Equation (14). Mean atomic number $<Z>$ and mean atomic weight $<A>$ are acquired by calculating using the chemical composition ratio in each pixel. An image relating to electron density ($\rho_e$) is acquired by calculating using $\delta$ acquired in Step S202 and Equation (15). In addition, an image relating to mass absorption coefficient ($\mu/\rho$) is acquired by using the acquired chemical composition ratio and Equation (4).

Tomographic images relating to the amount of each element based on the mass absorption coefficient, mass density, electron density, mean atomic number, mean atomic weight and chemical composition ratio of a detected object calculated with the arithmetic processing apparatus 113 can be displayed on the display device 114. A PC monitor, for example, can be used for the display device 114.

Furthermore, the configurations of each of the previously described embodiments and examples are merely intended to indicate a specific example of the present invention, and the scope of the present invention is not intended to be limited to only these configurations. For example, although X-rays were used in the above-mentioned embodiments, a detected object may also be measured using radiation other than X-rays. In addition, in the case of using a projection image for the measurement result as in the first embodiment, chemical composition ratio may be estimated with a search algorithm as was described in the second embodiment, or information relating to composition other than chemical composition ratio may be determined. In addition, although examples of detected objects having C, N, O and H as constituent elements thereof were indicated in the above-mentioned embodiments, the present invention can also be applied to other compounds.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-121637 filed on Jun. 12, 2014 which is hereby incorporated by reference herein in its entirety.

REFERENCE SIGNS LIST

100: X-ray measurement system
106: Detected object
113: Arithmetic processing apparatus
117: X-ray measurement apparatus

The invention claimed is:
1. An object information acquisition method for acquiring information relating to a composition of a detected object from results of a measurement using radiation, the method comprising:
a step of acquiring by a computer a result of measuring the detected object using radiation;
a step of estimating by a computer a chemical composition ratio of the detected object, using an equation that contains a value derived from the measurement result as a constant and contains a value derived from the chemical composition ratio of the detected object as a variable, and then solving the equation; and
a step of outputting the estimated chemical composition ratio or a physical property value acquired based on the estimated chemical composition ratio as information relating to the composition of the detected object,
wherein the value derived from the measurement result includes an absorption characteristic value, which is a value relating to absorption characteristics of the detected object with respect to radiation, and a phase characteristic value, which is a value relating to refraction characteristics of the detected object with respect to radiation, and
wherein the step of estimating the chemical composition ratio of the detected object comprises:

a step of setting a plurality of candidates for the chemical composition ratio, and a step of estimating the chemical composition ratio of the detected object by a procedure in which an approximate solution of the equation is determined from among the plurality of candidates.

2. The object information acquisition method according to claim 1, wherein the physical property value is at least any of mass density, mass absorption coefficient, effective atomic number, mean atomic weight, mean atomic number and electron density.

3. The object information acquisition method according to claim 1, wherein the information relating to the composition of the detected object is output in the form of image data indicating the distribution of chemical composition ratio or physical property values in the detected object.

4. The object information acquisition method according to claim 1, wherein a condition to be satisfied by the chemical composition ratio of the detected object is set in advance, and in the step of setting the plurality of candidates for chemical composition ratio, chemical composition ratios that do not satisfy the condition are excluded from consideration as candidates.

5. The object information acquisition method according to claim 1, wherein the radiation is in the form of X-rays or γ-rays.

6. The object information acquisition according to claim 5, wherein the equation is: [Math 1]

[Math. 1]

$$\frac{\mu t}{\phi} = \frac{1}{r_0 \lambda} \frac{\sigma_a}{\langle Z \rangle} \quad (6)$$

where
- $\mu$: linear absorption coefficient;
- $t$: optical path length of radiation inside of a detected object,
- $\phi$: amount of phase shift,
- $r_0$: classical electron radius,
- $\lambda$: radiation wavelength,
- $\sigma_a$: photon interaction cross-section per atom, and
- $\langle Z \rangle$: mean atomic number, wherein $\mu t$ and $\phi$ are constants derived from measurement results, and $\sigma_a$ and $\langle Z \rangle$ are variable derived from chemical composition ratio.

7. The object information acquisition method according to claim 4, wherein in the step of estimating the chemical composition ratio of the detected object, a chemical composition ratio, in which an evaluation value defined using a difference between the value on the left side of Equation (6) and the value on the right side of Equation (6) is equal to or less than a threshold value, is determined to be the chemical composition ratio of the detected object.

8. The object information acquisition according to claim 5, wherein the equation is:

[Math. 2]

$$\begin{cases} \rho_\beta = \beta / \left( \frac{\lambda}{4\pi} N_A \frac{\sigma_a}{\langle A \rangle} \right) \\ \rho_\delta = \delta / \left( \frac{r_0 \lambda^2 N_A}{2\pi} \frac{\langle Z \rangle}{\langle A \rangle} \right) \\ \rho_\beta = \rho_\delta \end{cases} \quad (11)$$

or

[Math. 3]

$$\frac{\beta}{\delta} = \frac{1}{2\lambda r_0} \frac{\sigma_a}{\langle Z \rangle} \quad (16)$$

Where
- $\beta$: imaginary component of complex refractive index ($n=1-\delta-i\beta$),
- $\delta$: part of real component of complex refractive index ($n=1-\delta-i\beta$),
- $\rho_\beta$: mass density as calculated from $\beta$,
- $\rho_\delta$: mass density as calculated from $\delta$,
- $\lambda$: radiation wavelength,
- $N_A$: Avogadro's number
- $\sigma_a$: photon interaction cross-section per atom,
- $\langle Z \rangle$: mean atomic number, and
- $\langle A \rangle$: mean atomic weight;

wherein $\beta$ and $\delta$ are constants derived from measurement results, and $\sigma_a$, $\langle Z \rangle$ and $\langle A \rangle$ are variables derived from a chemical composition ratio.

9. The object information acquisition method according to claim 6, wherein, in the step of estimating the chemical composition ratio of the detected object, a chemical composition ratio, in which an evaluation value defined using a difference between a value on the left side and a value on the right side of Equation (16), an evaluation value defined using a difference between a value of $\rho\beta$ determined in the first equation of Equation (11) and a value of $\rho\delta$ determined in the second equation of Equation (11), or the sum of these two evaluation values, is equal to or less than a threshold value, is determined to be the chemical composition ratio of the detected object.

10. The object information acquisition method according to claim 1, wherein the procedure is performed using an evaluation function for evaluating errors of the plurality of candidates.

11. A non-transitory computer-readable storage medium storing a program that executes, by a computer, each step of an object information acquisition method for acquiring information relating to a composition of a detected object from results of a measurement using radiation, the method comprising:

a step of acquiring by a computer a result of measuring the detected object using radiation;

a step of estimating by a computer a chemical composition ratio of the detected object, using an equation that contains a value derived from the measurement result as a constant and contains a value derived from the chemical composition ratio of the detected object as a variable, and then solving the equation; and a step of outputting the estimated chemical composition ratio or a physical property value acquired based on the estimated chemical composition ratio as information relating to the composition of the detected object, wherein the value derived from the measurement result includes an absorption characteristic value, which is a value relating to absorption characteristics of the detected object with respect to radiation, and a phase characteristic value, which is a value relating to refraction characteristics of the detected object with respect to radiation, and wherein the step of estimating the chemical composition ratio of the detected object comprises:

a step of setting a plurality of candidates for the chemical composition ratio, and a step of estimating the chemical composition ratio of the detected object by a procedure in which an approximate solution of the equation is determined from among the plurality of candidates.

12. An object information acquisition apparatus for acquiring information relating to a composition of a detected object from a result of a measurement using radiation, the apparatus comprising:

an acquisition unit that acquires a result of measuring the detected object, using radiation;

an estimation unit that estimates a chemical composition ratio of the detected object, using an equation that contains a value derived from the measurement result as a constant and contains a value derived from the chemical composition ratio of the detected object as a variable, and then solves the equation; and an output unit that outputs the estimated chemical composition ratio or a physical property value acquired based on the estimated chemical composition ratio as information relating to the composition of the detected object, wherein the value derived from the measurement result includes an absorption characteristic value, which is a value relating to absorption characteristics of the detected object with respect to radiation, and a phase characteristic value, which is a value relating to refraction characteristics of the detected object with respect to radiation, and wherein the estimation unit is configured to set a plurality of candidates for the chemical composition ratio and to perform a procedure in which an approximate solution of the equation is determined from among the plurality of candidates.

13. A system comprising: a measurement apparatus that measures a detected object, using radiation; the object information acquisition apparatus according to claim 11, which acquires information relating to the composition of the detected object, using the measurement result of the measurement apparatus; and a display device configured to display a tomographic image relating to the information relating to the composition of the detected object.

14. The object information acquisition apparatus according to claim 11, wherein the procedure is performed using an evaluation function for evaluating errors of the plurality of candidates.

15. An object information acquisition method for acquiring information relating to a composition of a detected object from a measurement result of the detected object acquired by irradiating the detected object with X-rays and detecting the X-rays that pass through the detected object, the method comprising:

a step of acquiring by a computer a result of measuring the detected object using X-rays;

a step of estimating by a computer a chemical composition ratio of the detected object, using an equation that contains a value derived from the measurement result as a constant and contains a value derived from the chemical composition ratio of the detected object as a variable, and then solving the equation; and a step of outputting the estimated chemical composition ratio or a physical property value acquired based on the estimated chemical composition ratio as information relating to the composition of the detected object, and wherein the step of estimating the chemical composition ratio of the detected object comprises:

a step of setting a plurality of candidates for the chemical composition ratio, and a step of estimating the chemical composition ratio of the detected object by a procedure in which an approximate solution of the equation is determined from among the plurality of candidates.

16. The object information acquisition method according to claim 15, wherein the procedure is performed using an evaluation function for evaluating errors of the plurality of candidates.

17. A system comprising:

a measurement apparatus that measures a detected object by irradiating the detected object with X-rays and detecting the X-rays that pass through the detected object; and an object information acquisition apparatus that acquires information relating to a composition of the detected object, using a measurement result of the measurement apparatus, wherein the object information acquisition apparatus has:

an acquisition unit that acquires the result of measuring the detected object using X-rays;

an estimation unit that estimates a chemical composition ratio of the detected object, using an equation that contains a value derived from the measurement result as a constant and contains a value derived from the chemical composition ratio of the detected object as a variable, and then solves the equation; and an output unit that outputs the estimated chemical composition ratio or a physical property value acquired based on the estimated chemical composition ratio as information relating to the composition of the detected object, and wherein the estimation unit is configured to set a plurality of candidates for the chemical composition ratio and to perform a procedure in which an approximate solution of the equation is determined from among the plurality of candidates.

18. The system according to claim 10, wherein the procedure is performed using an evaluation function for evaluating errors of the plurality of candidates.

* * * * *